United States Patent
Fukuda

(10) Patent No.: US 8,999,693 B2
(45) Date of Patent: Apr. 7, 2015

(54) METHOD FOR PRODUCING β-GLUCANASE AND XYLANASE, AND LIQUID CULTURE MEDIUM

(75) Inventor: Kazuro Fukuda, Moriya (JP)

(73) Assignee: Asahi Group Holdings, Ltd., Tokyo (JP)

( * ) Notice: Subject to any disclaimer, the term of this patent is extended or adjusted under 35 U.S.C. 154(b) by 0 days.

(21) Appl. No.: 13/139,663

(22) PCT Filed: Dec. 17, 2008

(86) PCT No.: PCT/JP2008/072981
§ 371 (c)(1),
(2), (4) Date: Jun. 14, 2011

(87) PCT Pub. No.: WO2010/070748
PCT Pub. Date: Jun. 24, 2010

(65) Prior Publication Data
US 2011/0244527 A1    Oct. 6, 2011

(51) Int. Cl.
| | |
|---|---|
| C12P 19/02 | (2006.01) |
| C12N 9/24 | (2006.01) |
| C12N 1/22 | (2006.01) |
| C12N 1/14 | (2006.01) |
| C12P 19/14 | (2006.01) |
| C12N 9/42 | (2006.01) |

(52) U.S. Cl.
CPC ........ *C12N 9/248* (2013.01); *C12N 1/14* (2013.01); *C12P 19/14* (2013.01); *C12Y 302/01006* (2013.01); *C12N 9/2437* (2013.01); *C12N 9/244* (2013.01)

(58) Field of Classification Search
CPC ........ C12P 19/14; C12N 9/244; C12N 9/248; C12N 9/2437
USPC .......................................... 435/105, 200, 252
See application file for complete search history.

(56) References Cited

U.S. PATENT DOCUMENTS 5,981,233 A    11/1999    Ringpfeil

FOREIGN PATENT DOCUMENTS

| CN | 1385519 A | 12/2002 |
|---|---|---|
| JP | 9-163980 A | 6/1997 |
| JP | 11-113568 A | 4/1999 |

OTHER PUBLICATIONS

International Search Report issued on Mar. 31, 2009 for counterpart application PCT/JP2008/072981.
U. Viesturs et al., "Production of Cellulases and Xylanases by Trichoderma viride and Biological Processing of Lignocellulose and Recycled Paper Fibers," Applied Biochemistry and Biotechnology, 1996, vol. 57/58, pp. 349-360.
R. Haapala et al., "Production of endo-1,4-beta-glucanase and xylanase with nylon-web immobilized and free *Trichoderma reesei*," Enyzyme and Microbial Technology, 1996, vol. 18, No. 7, pp. 495-501.
I. Seyis et al., "Effect of carbon and nitrogen sources on xylanase production by *Trichoderma harzianum* 1073 D3," International Biodeteriation & Biodegratation, 2005, vol. 55, pp. 115-119.
L. K. Ju et al.; "Wastepaper Hydrolysate as Soluble Inducing Substrate for Cellulase Production in Continuous Culture of *Trichoderma reesi*," Biotechnological Progress, 1999, vol. 15, pp. 91-97.
A. Ahamed et al., "Culture-based strategies to enhance cellulase enzyme production from *Trichoderma reesi* RUT-C30 in bioreactor culture conditions," Biochemical Engineering Journal, Jun. 1, 2008, vol. 40, pp. 399-407.
C. S. Shin et al., "Enzyme Production of *Trichoderma reesi* RUT C-30 on Various Lignocellulosic Substrates," Applied Biochemistry and Biotechnology, 2000, vol. 84-86, pp. 237-245.
Japanese Office Action dated Mar. 31, 2009, issued in corresponding Japanese Patent Application No. 2009-500640.
Office Action issued in counterpart European Patent Application No. 08878916.9, dated Feb. 14, 2014.
Extended European Search Report issued Jul. 17, 2013, in corresponding European Patent Application No. 08878916.9.
Gu Sai-Hong et al., "Effects of fermentation condiation on production of ?-glucanase and xylanase by *Trichoderma reesei*", Journal of Zhejiang University, Agriculture and Life Sciences, China, vol. 29, No. 5, May 1, 2003, pp. 545-549, XP009165593.
Office Action issued in corresponding Chinese Patent Application No. 200880132378.X on Feb. 8, 2013.
Communication dated Jul. 7, 2014 from the European Patent Office in counterpart European Patent Application No. 08878916.9.
Chen et al., "Cellulase Production Induced by Carbon Sources Derived from Waste Newspaper", Process Biochemistry, vol. 26(2), Apr. 1, 1991, pp. 93-100.
Chinese Office Action dated Aug. 5, 2013, issued in Chinese Patent Application No. 200880132378.X.

*Primary Examiner* — Tekchand Saidha
*Assistant Examiner* — MD. Younus Meah
(74) *Attorney, Agent, or Firm* — Sughrue Mion, PLLC

(57) ABSTRACT

A method for producing β-glucanase and xylanase which includes the step of culturing a microorganism classified under the genus *Trichoderma* using a liquid culture medium which contains (a) a pulp derived from paper which has not been subjected to heat treatment nor alkali treatment as a carbon source, and (b) an ammonia nitrogen or an amino nitrogen as a nitrogen source.

8 Claims, 25 Drawing Sheets

METHOD FOR PRODUCING β-GLUCANASE AND XYLANASE, AND LIQUID CULTURE MEDIUM

CROSS REFERENCE TO RELATED APPLICATION

This application is a National Stage of International Application No. PCT/JP2008/072981, filed on Dec. 17, 20089, the contents of all of which are incorporated herein by reference in their entirety.

TECHNICAL FIELD

The present invention relates to a method for producing β-glucanase and xylanase, and a liquid culture medium.

BACKGROUND ART

In order to efficiently utilize cellulosic resources, a method for efficiently decomposing cellulose has been explored in recent years. Cellulose is mainly decomposed by microorganism in nature, and it is known that various microorganisms such as bacteria and fungi produce cellulolytic enzymes.

These microorganisms secrete the cellulolytic enzymes outside those body, and cellulose is decomposed by its action into glucose via mainly cello-oligosaccharide and cellobiose. Cellulolytic enzymes are generally called as cellulase.

When cellulase is intended to artificially be produced, the genus *Trichoderma* is known as a microorganism secreting cellulase and is widely utilized. Moreover, a method for secreting cellulase by culturing the microorganisms classified under the genus *Trichoderma* using a culture medium containing nutrients such as carbon sources and nitrogen sources is also known.

However, in the conventional method for producing cellulase, materials usable as a carbon source are limited. For example, crystalline celluloses are expensive. Even if there are cellulosic resources which are inexpensive, they generally require pretreatments such as heat treatment or alkali treatment, and cause relatively high cost.

For example, Patent Literature 1 discloses a substrate for producing cellulase capable of inoculating cellulase-producing microorganisms by boiling used paper in a ferrous sulfate solution. In addition, Patent Literature 2 discloses a method for producing a substrate for producing cellulase capable of inoculating *Trichoderma reesei* which is cellulase-producing microorganisms by boiling finely-milled bagasse with caustic alkali and treating with a hypochlorite solution.

In addition, the cellulase obtained by these conventional methods mainly contains β-glucanase, has low xylanase activity, and is poor in ability to decompose a cellulosic resource containing xylan, such as bagasse and rice straw. Therefore, it is less effective for the purpose of efficiently utilizing naturally-occurring various cellulosic resources.

Patent Literature 3 discloses a method for producing xylanase by culturing a microorganism classified under the genus *Trichoderma* by using a diluted alcohol distillation waste fluid of rye subjected to preliminary treatment such as removal of solid constituents, concentration of nonvolatile components or autoclave treatment of the concentrate.

However, rye used as a carbon source in this technology is difficult to obtain, and it requires complicated pretreatment and causes high cost. In addition, production amount of β-glucanase even more decreases in this method.

Non Patent Literature 1 shows that productivity of cellulase is low in the test of enzyme production by *Trichoderma reesei* using paper (newspaper and office paper) which has not been subjected to pretreatment such as heat treatment or alkali treatment.

It has never been known a successful example which can highly produce β-glucanase and xylanase at the same time using paper which has not been subjected to heat treatment nor alkali treatment as a cellulosic resource.

[Patent Literature 1] Japanese Patent Laid-open Publication No. 2003-137901
[Patent Literature 2] Japanese Patent Publication No. H5 (1993)-33984
[Patent Literature 3] Japanese Patent Laid-open Publication No. H11 (1999)-113568
[Non Patent Literature 1] Applied Biochemistry and Biotechnology pp. 237-245, Vol. 84-86, 2000

DISCLOSURE OF THE INVENTION

Problems to be Solved by the Invention

The present invention solves the above conventional problems, and the objective thereof is to produce cellulase which has excellent ability for decomposing a cellulosic resource containing xylan at low cost.

Means for Solving the Problem

The present invention provides a method for producing β-glucanase and xylanase comprising the step of culturing a microorganism classified under the genus *Trichoderma* by using a liquid culture medium which contains (a) a pulp derived from paper which has not been subjected to heat treatment nor alkali treatment as a carbon source and (b) an ammonia nitrogen or an amino nitrogen as a nitrogen source.

In one embodiment, the initial concentration of the pulp in the liquid culture medium is not less than 2% W/V.

In one embodiment, the initial concentration of the pulp in the liquid culture medium is from 2 to 7% W/V.

In one embodiment, the initial concentration of the ammonia nitrogen or amino nitrogen in the liquid culture medium is not less than 50 mM.

In one embodiment, the initial concentration of the ammonia nitrogen or amino nitrogen in the liquid culture medium is from 50 to 660 mM.

In one embodiment, the paper is at least one selected from the group consisting of high-quality paper, groundwood paper, copy paper, newspaper and cardboard.

In one embodiment, the microorganism classified under the genus *Trichoderma* is *Trichoderma reesei*.

In one embodiment, the pulp is added to the liquid culture medium in the course of culture.

In addition, the present invention provides a liquid culture medium comprising (a) a pulp derived from paper which has not been subjected to heat treatment nor alkali treatment as a carbon source and (b) an ammonia nitrogen or an amino nitrogen as a nitrogen source, wherein the liquid culture medium is used for culturing a microorganism classified under the genus *Trichoderma*.

In one embodiment, the pulp is contained in not less than 2% W/V.

In one embodiment, the ammonia nitrogen or amino nitrogen is contained in 50 to 660 mM.

In addition, the present invention provides a β-glucanase and xylanase produced according to any one of the above described methods.

In addition, the present invention provides a method for decomposing or glycosylating a cellulosic resource, characterized by using the β-glucanase and xylanase.

Effects of the Invention

In the present invention, since untreated papers can be used as a carbon source of a liquid culture medium, it is low cost and low energy and has a low impact on the environment. In addition, since β-glucanase and xylanase can be highly produced as cellulase at the same time, it is extremely useful for glycosylation of natural cellulosic resources containing xylan such as bagasse and rice straw. Specifically, it is useful for biomass ethanol production which produces ethanol from a cellulosic resource.

BEST EMBODIMENT FOR CARRYING OUT THE INVENTION

Liquid Culture Medium

The liquid culture medium of the present invention is a material containing nutrients which grow a microorganism classified under the genus *Trichoderma*. The liquid culture medium is prepared based on a liquid culture medium obtained by dissolving and suspending the following culture medium composition into 100 ml of water (generally called as Mandel medium), and contains a pulp as a carbon source and an ammonia nitrogen or an amino nitrogen as a nitrogen source. One example of a preferred medium composition is shown below.

Containing crystalline cellulose (manufactured by Fluka BioChemika, Trade-name: Avicel PH101): 1 g, $(NH_4)_2SO_4$: 0.14 g, $KH_2PO_4$: 1.5 g, $CaCl_2.2H_2O$: 0.03 g, $MgSO_4.7H_2O$: 0.03 g, corn steep liquor: 2 mL, Tween 80: 0.1 mL, trace element solution ($H_3BO_4$ 6 mg, $(NH_4)_6Mo_7O_{24}.4H_2O$ 26 mg, $FeCl_3.6H_2O$ 100 mg, $CuSO_4.5H_2O$ 40 mg, $MnCl_2.4H_2O$ 8 mg, $ZnSO_4.7H_2O$ 200 mg solution): 0.1 mL, and water: 100 mL (adjusted to pH 4.8 with phosphoric acid or sodium hydroxide)

The pulp refers to fibers used as a raw material for manufacturing paper. The type of the pulp is preferably a pulp with high cellulose purity such as chemical pulp and used paper pulp. The preferred pulp is a pulp derived from papers, which can be obtained by splitting and cutting papers.

Specific examples of the preferred paper include high-quality paper, groundwood paper, copy paper, newspaper, cardboard, and the like. The papers may be those which contain preferred pulp, and also may be a printed or written paper or a paper generally referred to as a used paper. For example, a page of paper from old book, magazine and well-worn notebook, flyer, envelope, writing paper, postcard, tissue paper, and the like can be also used.

The concentration of the pulp in the liquid culture medium is preferably not less than 2% W/V. When the concentration of the pulp is less than 2% W/V, production amount of cellulase, especially β-glucanase, may not increase so much.

The higher the concentration of the pulp in the liquid culture medium, the better. In other words, the upper limit is the amount of limit that can perform stirring and mixing of the liquid culture medium. In order to facilitate stirring and mixing of the liquid culture medium, it is preferred that the papers are cut with a shredder and used. For example, the upper limit of the initial concentration of the pulp in the liquid culture medium may be 20, 15 or 10% W/V depending on performance of a stirrer. Generally, the preferred range of the initial concentration of the pulp is from 2 to 7% W/V and preferably from 3 to 5% W/V.

The ammonia nitrogen refers to a nitrogen contained in ammonia or an ammonium salt derived from ammonia. In addition, the amino nitrogen refers to a nitrogen contained in amine or an amino compound derived from amine. Examples of the compound which contains an ammonia nitrogen or an amino nitrogen are ammonium sulfate, ammonium nitrate, diammonium phosphate, ammonium chloride, aqueous ammonia, urea, amino acid, and the salts thereof (for example, sodium glutamate).

Among these, the compound particularly preferable for using as a nitrogen source in the liquid culture medium of the present invention is ammonium sulfate. The reason is that it is low cost and easily available.

The concentration of the ammonia nitrogen or amino nitrogen in the liquid culture medium is from 35 to 660 mM as the number of moles of ammonium. Preferably, the concentration is from 50 to 580 mM. When the concentration is less than 35 mM, production amount of cellulase, especially β-glucanase, may not increase so much. In addition, when the initial concentration exceeds 660 mM, productivity of the enzymes decreases. In addition, it is preferable to increase or decrease concentration of the ammonia nitrogen or amino nitrogen in the liquid culture medium depending on concentration of the pulp in the liquid culture medium, and for example, when concentration of the pulp is 3% W/V, 50 mM is preferable when cost and the like are considered.

Method for Producing β-Glucanase and Xylanase

The fungi of the genus *Trichoderma* is known as microorganisms which produce cellulase required for glycosylation of cellulose. The microorganism classified under the genus *Trichoderma* used in the present invention is not particularly limited as long as it can produce cellulase. The preferred microorganism classified under the genus *Trichoderma* is *Trichoderma reesei* or *Trichoderma viride*. Particularly preferably, the microorganism is *Trichoderma reesei*.

Mycological properties of fungi *Trichoderma reesei* and *Trichoderma viride* are described in, for example, E. G. Simmons, Abst. 2nd International Mycological Congress, Tampa, Fla., U.S., August 1977, page 618.

A conventional aeration-agitation culture device is used for liquid culture, and it is cultured at a culture temperature of 20° to 33° C., and preferably 28° to 30° C., at a culture pH of 4 to 6 for 4 to 10 days, using the above described liquid culture medium. Pulp may be added to the liquid culture medium in the course of culture. It is because there may be a case that the production efficiency of cellulase improves by supplementing a carbon source since the pulp in the culture medium is decomposed with the progression of culture. When pulp is added, the form of addition may be continuous or batch, and the timing and amount of addition may be adjusted so that stirring and mixing is possible even after addition of the pulp.

When pulp is added, the ammonia nitrogen or amino nitrogen may be properly added as necessary.

Subsequently, if necessary, a fungus body is removed from this culture fluid by a known method such as centrifugation and filtration, to obtain culture supernatant fluid of the fungi of the genus *Trichoderma*. The culture fluid or culture supernatant fluid of the fungi of the genus *Trichoderma* contains the intended cellulase, in other words, β-glucanase and xylanase, in high concentration.

β-glucanase activity of the obtained culture fluid or culture supernatant fluid is not less than 30 U/ml, preferably not less than 50 U/ml, more preferably not less than 60 U/ml, and further preferably not less than 70 U/ml. Also, xylanase activity of the obtained culture fluid or culture supernatant fluid is not less than 25 U/ml, preferably not less than 30 U/ml, more preferably not less than 40 U/ml, and further preferably not less than 50 U/ml. When either β-glucanase activity or xylanase activity of the culture fluid or culture supernatant fluid decreases to less than the above lower limit, the effect on the purpose of efficiently utilizing naturally-occurring various cellulosic resources decreases.

The above hemicellulase activity can be quantitated based on the increase in absorbance at 540 nm by reacting a reducing sugar produced by enzymatic hydrolysis using oat spelts-derived xylan as a substrate with DNS.

More specifically, 0.1 ml of the culture fluid or culture supernatant fluid is added to 1.9 ml of a 1% xylan substrate solution (Xylan, from oat spelts, manufactured by Sigma is dissolved into 200 nM acetic acid buffer solution (pH 4.5)), and enzymatic reaction is performed accurately for 10 minutes at 40° C. Thereafter, 4 ml of a DNS reagent (containing 0.75% dinitrosalicylic acid, 1.2% sodium hydroxide, 22.5% potassium sodium tartrate tetrahydrate, and 0.3% lactose monohydrate) is added thereto and mixed well, to stop the reaction. In order to quantitate the amount of reducing sugar contained in the reaction stop solution, the reaction stop solution is heated in a boiling-water bath accurately for 15 minutes. Subsequently, the reaction stop solution is cooled to room temperature, and the absorbance at 540 nm is then determined to quantitate as the amount of reducing sugar corresponding to xylose. 1 unit of the hemicellulase activity is represented as the enzyme level which produces a reducing sugar corresponding to 1 µmol of xylose in 1 minute under the reaction conditions at 40° C. for 10 minutes.

Method for Decomposing or Glycosylating Cellulosic Resources

The β-glucanase and xylanase obtained by the method of the present invention are useful for decomposing or glycosylating cellulosic resources. The cellulosic resources referred herein may be either synthetic cellulose or natural cellulosic resources. The synthetic cellulose represents a cellulose distributed as cellulose powder. The natural cellulosic resources include bagasse, rice straw, wheat straw, beer draff, wood, and the like. The present invention can highly produce β-glucanase and xylanase at the same time and is therefore excellent, in particular, glycosylation of natural cellulosic resources such as bagasse, rice straw, wheat straw, and beer draff.

A known method may be used as the method for decomposing or glycosylating a cellulosic resource, and is not particularly limited. One example includes a method of suspending a cellulosic resource as a substrate in an aqueous medium, adding the above described culture fluid or culture supernatant fluid thereto, and heating while stirring or shaking, to perform a glycosylation reaction. In place of the above described culture fluid or culture supernatant fluid which shows cellulolytic activity, the dry matter thereof or a solution obtained by dispersing or dissolving the dry matter in water may be used.

It is preferred that the cellulosic raw material is preliminarily delignified. The reaction conditions such as suspending method, stirring method, method of adding the above mixed solution, order of addition, and concentrations thereof are properly adjusted so that glucose is obtained in higher yield.

The pH and temperature of the reaction solution at that time should be within the range that enzyme is not inactivated, and generally, when the reaction is carried out at ordinary pressure, the temperature should be in the range of 30 to 70° C. and pH should be in the range of 3 to 7. In addition, while the pressure, temperature and pH are also properly adjusted so that glucose is obtained in higher yield as described above, it is preferred to carry out in an acetic acid- or phosphate-buffer solution at ordinary pressure at a temperature in the range of 50° to 60° C. and a pH in the range of 4 to 6. The reaction time is generally from 6 to 147 hours, and preferably from 24 to 72 hours.

An aqueous solution containing glucose is obtained by glycosylation of cellulose. The obtained aqueous solution can be subjected to purification treatment such as decolorization, desalination, and enzyme removal as necessary. The purification method is not particularly limited as long as it is a known method, and for example, activated carbon treatment, ion-exchange resin treatment, chromatography treatment, filtration treatments such as microfiltration, ultrafiltration and reverse osmosis filtration, crystallization treatment, and the like may be used, and these methods may be used alone or in combination of 2 or more kinds.

The aqueous solution mainly composed of a glucose purified by the above method can be used as it is, and may be solidified by drying as necessary. The drying method is not particularly limited as long as it is a known method, and for example, spray drying, freeze drying, drum drying, thin-film drying, tray drying, flash drying, vacuum drying, and the like may be used, and these methods may be used alone or in combination of 2 or more kinds.

EXAMPLES

Hereinafter, the present invention will be more specifically described by reference to Examples, but the present invention is not limited to these examples.

Example 1

*Trichoderma reesei* QM9414 (NBRC 31329) was cultured on a potato dextrose agar medium at 28° C. for 7 days, to sufficiently form spores. Crystalline cellulose, a carbon source of Mandel medium, was replaced with 3% of copy paper (3 g/100 ml), and ammonium sulfate, a nitrogen source, was added so that the molar concentration of ammonia nitrogen became each 15 mM, 35 mM, 50 mM, 65 mM, 80 mM, 100 mM or 115 mM and adjusted to pH 4.8 with phosphoric acid and sodium hydroxide, to prepare 100 ml of a liquid culture medium in a 500-ml volume Erlenmeyer flask with baffles. One loopful of the cultured *Trichoderma reesei* was inoculated in this liquid culture medium and cultured with shaking at 28° C., 180 rpm for 7 days. The culture fluid was centrifuged on day 7, and β-glucanase activity and xylanase activity of the supernatant fluid were determined. The copy paper was not subjected to pretreatment such as alkali treatment or heat treatment, and was only cut into 2 mm×7 mm with a shredder (desk purser DS-4100 by CARL) and used.

(Determination of Enzyme Activity)

The enzyme activity was determined for the culture fluid obtained above.

For β-glucanase activity, the absorbance of a dyed fragment generated by enzymatic decomposition using dye-labeled β-glucan as a substrate was determined using a β-glucanase assay kit manufactured by Megazyme. Specifically, 0.1 ml of the culture fluid was added to 0.1 ml of azo-barley glucan substrate solution, and enzymatic reaction was performed accurately for 10 minutes at 40° C. Thereafter, 0.6 ml of a stop solution [containing 4% sodium acetate, 0.4% zinc acetate, and 80% methyl cellosolve (pH 5)] was added thereto and left for 5 minutes to stop the reaction. Subsequently, the solution was centrifuged, and thereafter the absorbance at 590 nm of the supernatant fluid was determined. 1 unit of the β-glucanase activity was represented as the enzyme level which produces a reducing sugar corresponding to 1 μmol of glucose in 1 minute under the reaction conditions at 40° C. for 10 minutes.

Next, the xylanase activity was quantitated by the increase in absorbance at 540 nm by reacting a reducing sugar produced by enzymatic hydrolysis using oat spelts-derived xylan as a substrate with DNS. More specifically, 0.1 ml of the culture fluid was added to 1.9 ml of a 1% xylan substrate solution [Xylan, from oat spelts, manufactured by Sigma was dissolved into 200 mM acetic acid buffer solution (pH 4.5)], and enzymatic reaction was performed accurately for 10 minutes at 40° C. Thereafter, 4 ml of a DNS reagent (containing 0.75% dinitrosalicylic acid, 1.2% sodium hydroxide, 22.5% potassium sodium-tartrate tetrahydrate, and 0.3% lactose monohydrate) was added thereto and mixed well, to stop the reaction. In order to quantitate the amount of reducing sugar contained in the reaction stop solution, the reaction stop solution was heated in a boiling-water bath accurately for 15 minutes. Subsequently, the reaction stop solution was cooled to room temperature, and the absorbance at 540 nm was then determined to quantitate as the amount of reducing sugar corresponding to xylose. 1 unit of the xylanase activity was represented as the enzyme level which produces a reducing sugar corresponding to 1 μmol of xylose in 1 minute under the reaction conditions at 40° C. for 10 minutes. The results are shown in FIG. 1.

Example 2

According to the same manner as in Example 1, 3% of cardboard (3 g/100 ml) was employed instead of the crystalline cellulose, a carbon source of Mandel medium, to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 2.

Example 3

According to the same manner as in Example 1, 3% of newspaper (3 g/100 ml) was employed instead of the crystalline cellulose, a carbon source of Mandel medium, to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and O-glucanase activity and xylanase activity were determined in the same manner as in Example 1. The results are shown in FIG. 3.

Example 4

According to the same manner as in Example 1, 3% of copy paper (3 g/100 ml) was employed instead of the crystalline cellulose, a carbon source of Mandel medium, and ammonium chloride instead of the ammonium sulfate, a nitrogen source, was added so that the molar concentration of ammonia nitrogen became each 20 mM, 40 mM, 50 mM, 60 mM, 80 mM, 100 mM or 120 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 4.

Example 5

According to the same manner as in Example 1, 3% of copy paper (3 g/100 ml) was employed instead of the crystalline cellulose, a carbon source of Mandel medium, and diammonium phosphate instead of the ammonium sulfate, a nitrogen source, was added so that the molar concentration of ammonia nitrogen became each 15 mM, 35 mM, 50 mM, 65 mM, 80 mM, 100 mM or 115 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 5.

Example 6

According to the same manner as in Example 1, 3% of copy paper (3 g/100 ml) was employed instead of the crystalline cellulose, a carbon source of Mandel medium, ammonium nitrate instead of the ammonium sulfate, a nitrogen source, was added so that the molar concentration of ammonia nitrogen became each 12 mM, 24 mM, 36 mM, 48 mM, 60 mM, 72 mM or 84 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 6.

Example 7

According to the same manner as in Example 1, 3% of copy paper (3 g/100 ml) was employed instead of the crystalline cellulose, a carbon source of Mandel medium, and aqueous ammonia instead of the ammonium sulfate, a nitrogen source, was added so that the molar concentration thereof became each 15 mM, 30 mM, 45 mM, 65 mM, 75 mM, 90 mM or 105 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 7.

Example 8

According to the same manner as in Example 1, 3% of copy paper (3 g/100 ml) was employed instead of the crystalline cellulose, a carbon source of Mandel medium, and urea instead of the ammonium sulfate, a nitrogen source, so that the molar concentration of ammonia nitrogen became each 17 mM, 33 mM, 50 mM, 67 mM, 83 mM or 100 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 8.

Example 9

According to the same manner as in Example 1, copy paper instead of the crystalline cellulose, a carbon source of Mandel medium, was added so that the concentration thereof became 1%, 2%, 3%, 4%, 5%, 6%, or 7%, and the ammonium sulfate, a nitrogen source, was added so that the molar concentration of ammonia nitrogen became 80 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 9.

Example 10

According to the same manner as in Example 1, copy paper instead of the crystalline cellulose, a carbon source of Mandel medium, was added so that the concentration thereof became 1%, 2%, 3%, 4%, 5%, 6%, or 7%, and the ammonium sulfate, a nitrogen source, was added so that the molar concentration of ammonia nitrogen became 160 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 10.

Example 11

According to the same manner as in Example 1, copy paper instead of the crystalline cellulose, a carbon source of Mandel medium, was added so that the concentration thereof became 1%, 2%, 3%, 4%, 5%, 6%, or 7%, and the ammonium sulfate, a nitrogen source, was added so that the molar concentration of ammonia nitrogen became 320 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 11.

Example 12

According to the same manner as in Example 1, copy paper instead of the crystalline cellulose, a carbon source of Mandel medium, was added so that the concentration thereof became 1%, 2%, 3%, 4%, 5%, 6%, or 7%, and the ammonium sulfate, a nitrogen source, was added so that the molar concentration of ammonia nitrogen became 480 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 12.

Reference Example 1

According to the same manner as in Example 1, concentration of the crystalline cellulose, a carbon source of Mandel medium, was adjusted to 1%, and the ammonium sulfate, a nitrogen source, was added so that the molar concentration of ammonia nitrogen became each 15 mM, 35 mM, 50 mM, 65 mM, 80 mM, 100 mM or 115 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 13.

Reference Example 2

According to the same manner as in Example 1, the crystalline cellulose, a carbon source of Mandel medium, was added so that the concentration thereof became 1%, 1.5%, 2%, 2.5%, 3%, 3.5%, or 4%, and the ammonium sulfate, a nitrogen source, was added so that the molar concentration of ammonia nitrogen became 160 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 14.

Reference Example 3

According to the same manner as in Example 1, 1% of copy paper (3 g/100 ml) was added instead of the crystalline cellulose, a carbon source of Mandel medium, and the ammonium sulfate, a nitrogen source, was added so that the molar concentration of ammonia nitrogen became each 15 mM, 35 mM, 50 mM, 65 mM, 80 mM, 100 mM or 115 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 15.

Reference Example 4

According to the same manner as in Example 1, 3% of copy paper (3 g/100 ml) was added instead of the crystalline cellulose, a carbon source of Mandel medium, and potassium nitrate instead of the ammonium sulfate, a nitrogen source, was added so that the molar concentration of ammonia nitrogen became each 10 mM, 20 mM, 30 mM, 40 mM, 50 mM, 60 mM or 70 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 16.

Example 13

*Trichoderma reesei* QM9414 (NBRC 31329) was cultured on a potato dextrose agar medium at 28° C. for 7 days, to sufficiently form spores. One loopful thereof was inoculated in a 500-ml volume Erlenmeyer flask with baffles which contains 100 ml of Mandel medium and cultured with shaking at 28° C., 180 rpm for 4 days. It was inoculated in a 500-ml volume Erlenmeyer flask with baffles which contains 150 ml of Mandel medium and cultured with shaking at 28° C., 180 rpm for 2 days, to obtain a culture fluid. 3 L of a culture medium obtained by adding 3% (30 g/l), 6% (60 g/l) of copy paper or 3% of crystalline cellulose (Avicel PH101) instead of the crystalline cellulose, a carbon source of Mandel medium, adding the ammonium sulfate, a nitrogen source, so that the molar concentration of ammonia nitrogen became 200 mM, and employing 6 g/l of Adekanol LG-126 (manufactured by ADEKA CORPORATION) instead of Tween 80, and the culture fluid were added to a 5-L fermentor (manufactured by B.E. MARUBISHI CO., LTD.), and the mixture was cultured at 28° C. It was conducted with an aeration of 1 VVM and stirring at 450 rpm, and pH was adjusted with 2 N sodium hydroxide and five-fold diluted phosphoric acid so as to stay constant at pH 4.8 during the culture period. The culture fluid was centrifuged on day 7, and β-glucanase activity and xylanase activity of the supernatant fluid were determined. The results are shown in FIG. 17.

The copy paper was cut into 4 mm×30 mm with a shredder (Primo1400 manufactured by Meikoshokai Co., Ltd.) and used. In addition, 6% of copy paper (60 g/l) was added in total amount at one time, stirring became insufficient, and therefore, copy paper and ammonium sulfate were added in halves on day 1 and day 3 of the culture.

Example 14

According to the same manner as in Example 13, 6% of copy paper (60 g/l) was added to a 5-L fermentor, ammonium sulfate was added so that the molar concentration of ammonia nitrogen became 44 mM, 100 mM, 134 mM, or 224 mM, and production of the enzymes was examined. The results are shown in FIG. 18.

Example 15

According to the same manner as in Example 13, 6% of copy paper (60 g/l) and ammonium sulfate were added so that the molar concentration of ammonia nitrogen became 45 mM to a 5-L fermentor, and production of the enzymes were compared between the case that 2 N sodium hydroxide was employed as a chemical for adjusting pH during the culture period and the case that 18% aqueous ammonia was employed. Input amount of the aqueous ammonia during the culture period at that time was 123 mM. The results are shown in FIG. 19.

Example 16

According to the same manner as in Example 1, 3% of copy paper (3 g/100 ml) was employed instead of the crystalline cellulose, a carbon source of Mandel medium, and the ammonium sulfate, a nitrogen source, was added so that the molar concentration of ammonia nitrogen became each 330 mM, 420 mM, 500 mM, 580 mM, 660 mM, 720 mM or 800 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 20.

Example 17

According to the same manner as in Example 1, 3% of copy paper (3 g/100 ml) was employed instead of the crystalline cellulose, a carbon source of Mandel medium, and sodium glutamate instead of the ammonium sulfate, a nitrogen source, was added so that the molar concentration of amino nitrogen became each 17 mM, 33 mM, 50 mM, 67 mM, 83 mM or 100 mM to prepare a liquid culture medium. *Trichoderma reesei* QM9414 (NBRC 31329) was cultured on a potato dextrose agar medium at 28° C. for 7 days, to sufficiently form spores, and one loopful thereof was inoculated in the liquid culture medium and cultured with shaking at 28° C., 180 rpm for 7 days. The culture fluid was centrifuged on day 7, and β-glucanase activity and xylanase activity were determined in the same manner as in Example 1. The results are shown in FIG. 21.

Example 18

Glycosylation test of cellulosic resources was performed using each supernatant fluid of the culture medium with 6% of copy paper and the culture medium with 3% of crystalline cellulose obtained in Example 13. As the cellulosic resources subjected to glycosylation, cellulose powder (manufactured by NIPPON PAPER CHEMICALS CO., LTD., Tradename: KC FLOCK W-50), bagasse, rice straw, and beer draff were used. The bagasse, rice straw and beer draff were each finely milled, suspended in 0.3 N NaOH, treated at 120° C. for 15 minutes, sufficiently washed with water, thereafter dried, subjected to delignification treatment, and subjected to glycosylation. The cellulose powder was directly subjected to glycosylation. A solution (8% cellulosic resource solution) which was composed of the cellulosic resource: 0.8 g, the culture supernatant fluid: 9 ml, and 1 M acetic acid buffer (pH 4.8): 0.2 ml was shaken at 50° C., pH 4.8 for 48 hours to glycosylate, and the produced glucose was determined by Glucose CII-Test Wako (Wako Pure Chemicals). The results are shown in FIG. 22 to FIG. 25.

It was shown from the results of Examples and Reference Examples that *Trichoderma reesei* was cultured by using a liquid culture medium which contains untreated paper as a carbon source and contains ammonia/ammonium salt as a nitrogen source to produce β-glucanase and xylanase at the same time in high productivity. It was also shown that paper in the culture medium was increased in concentration to the level higher than that of a carbon source normally used, or ammonia/ammonium salt in the culture medium was adjusted in concentration to the specific range to increase production amount of the cellulase remarkably. It was also shown that various cellulosic resources can be decomposed and glycosylated by using the resulting culture supernatant fluid.

INDUSTRIAL APPLICABILITY

β-glucanase and xylanase that are extremely useful for, in particular, glycosylation of natural cellulosic resources such as bagasse and rice straw can be highly produced at the same time, and can be utilized for biomass ethanol production that produces ethanol from cellulosic resources.

Figure 1:
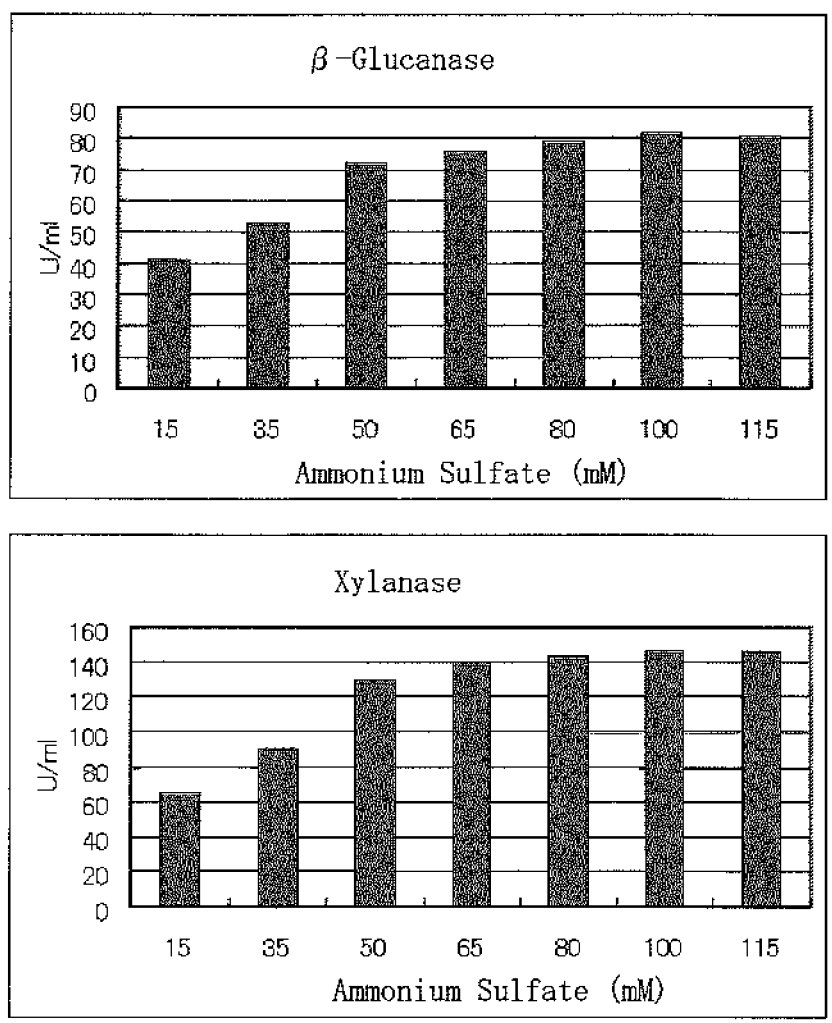
FIG. 1 A graph showing the change of enzyme activity of a culture supernatant fluid against the concentration of ammonium sulfate in a culture medium with 3% of copy paper.
Figure 2:
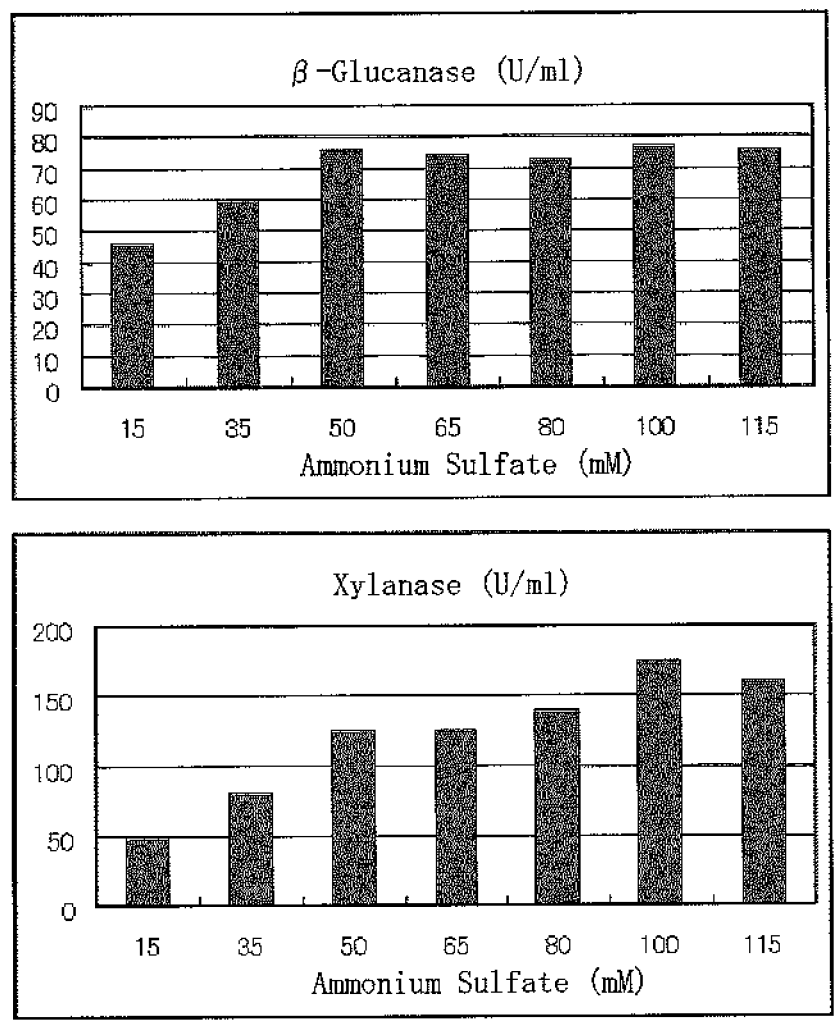
FIG. 2 A graph showing the change of enzyme activity of a culture supernatant fluid against the concentration of ammonium sulfate in a culture medium with 3% of cardboard.
Figure 3:
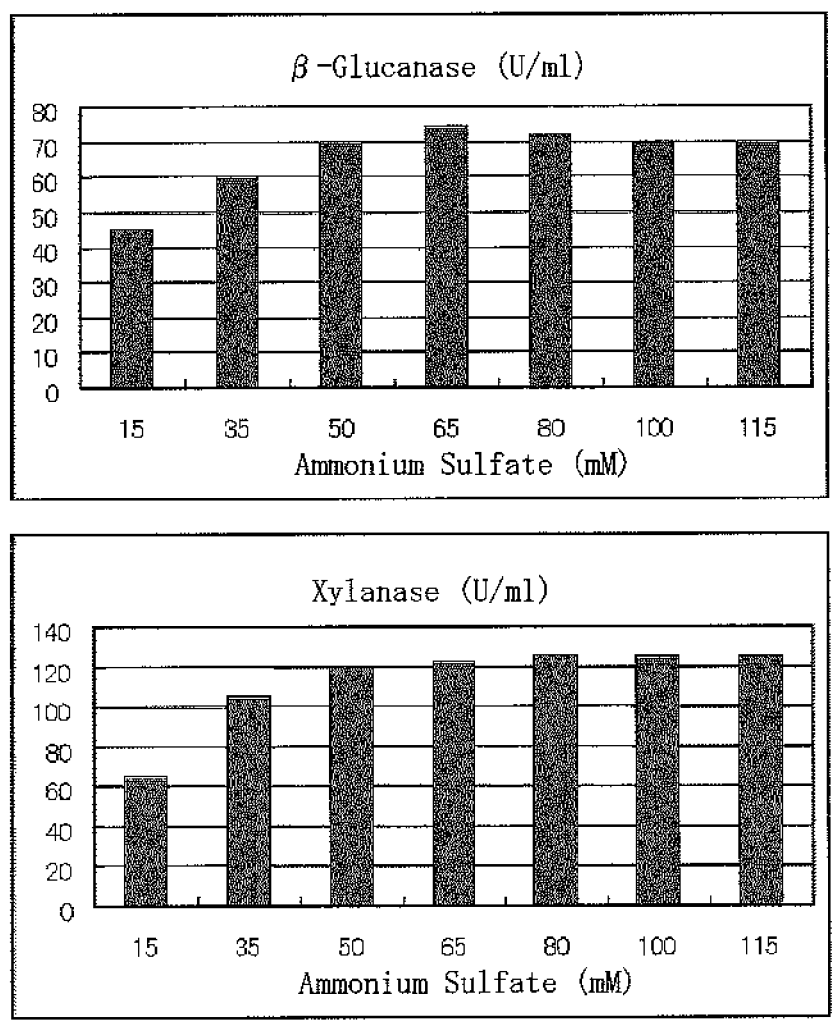
FIG. 3 A graph showing the change of enzyme activity of a culture supernatant fluid against the concentration of ammonium sulfate in a culture medium with 3% of newspaper.
Figure 4:
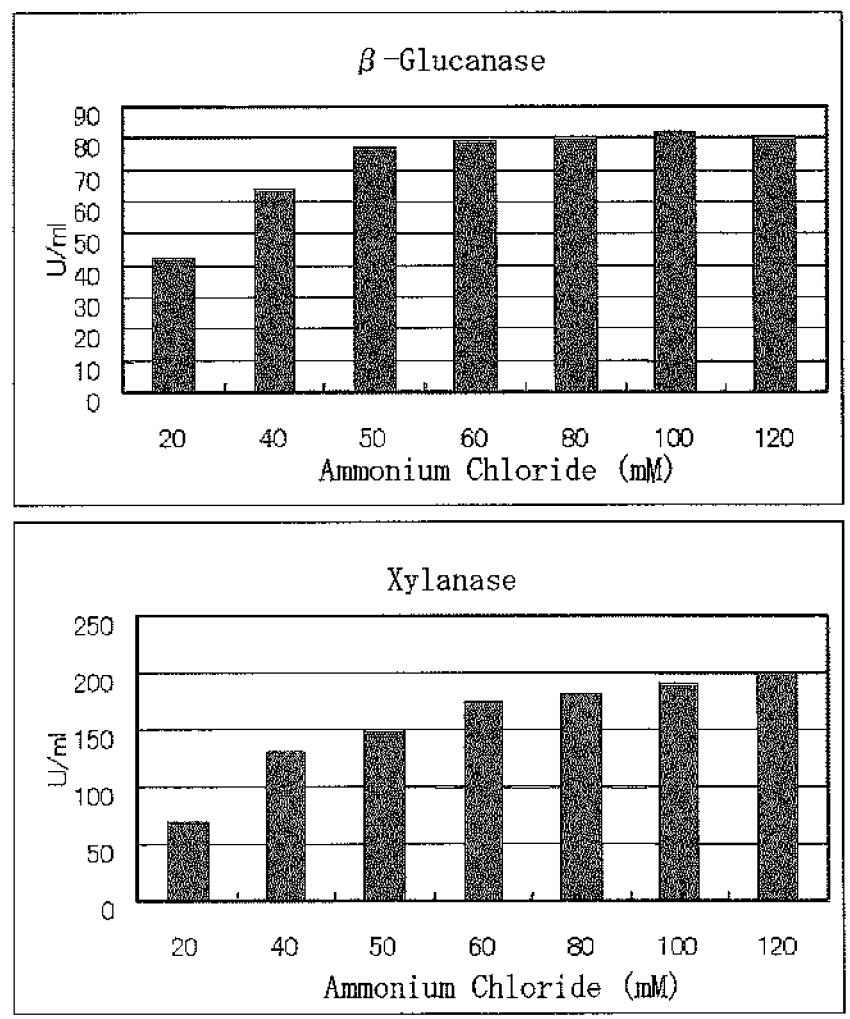
FIG. 4 A graph showing the change of enzyme activity of a culture supernatant fluid against the concentration of ammonium chloride in a culture medium with 3% of copy paper.
Figure 5:
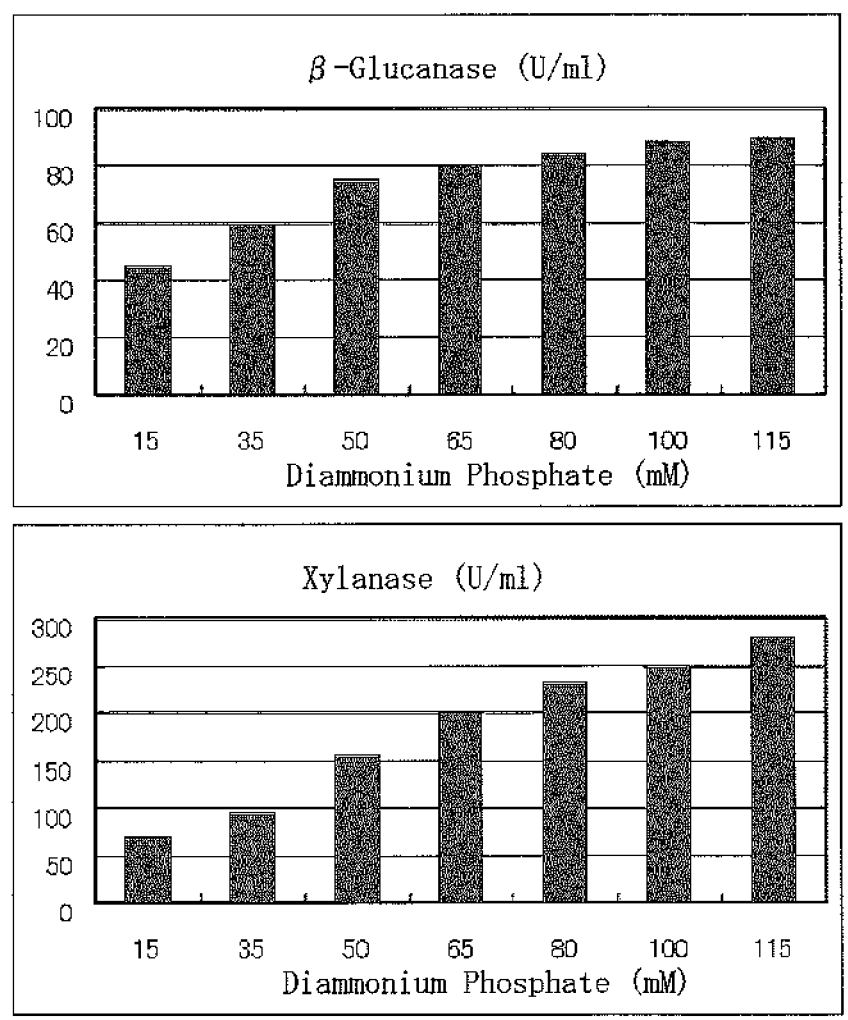
FIG. 5 A graph showing the change of enzyme activity of a culture supernatant fluid against the concentration of diammonium phosphate in a culture medium with 3% of copy paper.
Figure 6:
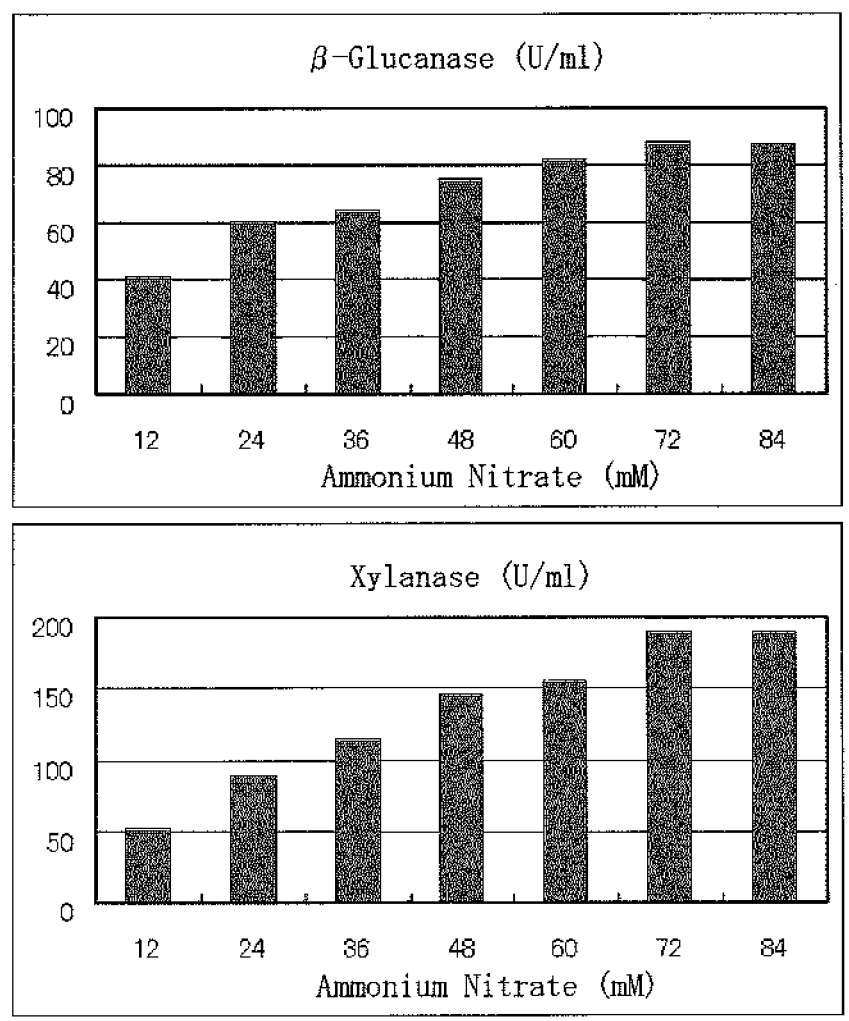
FIG. 6 A graph showing the change of enzyme activity of a culture supernatant fluid against the concentration of ammonium nitrate in a culture medium with 3% of copy paper.
Figure 7:
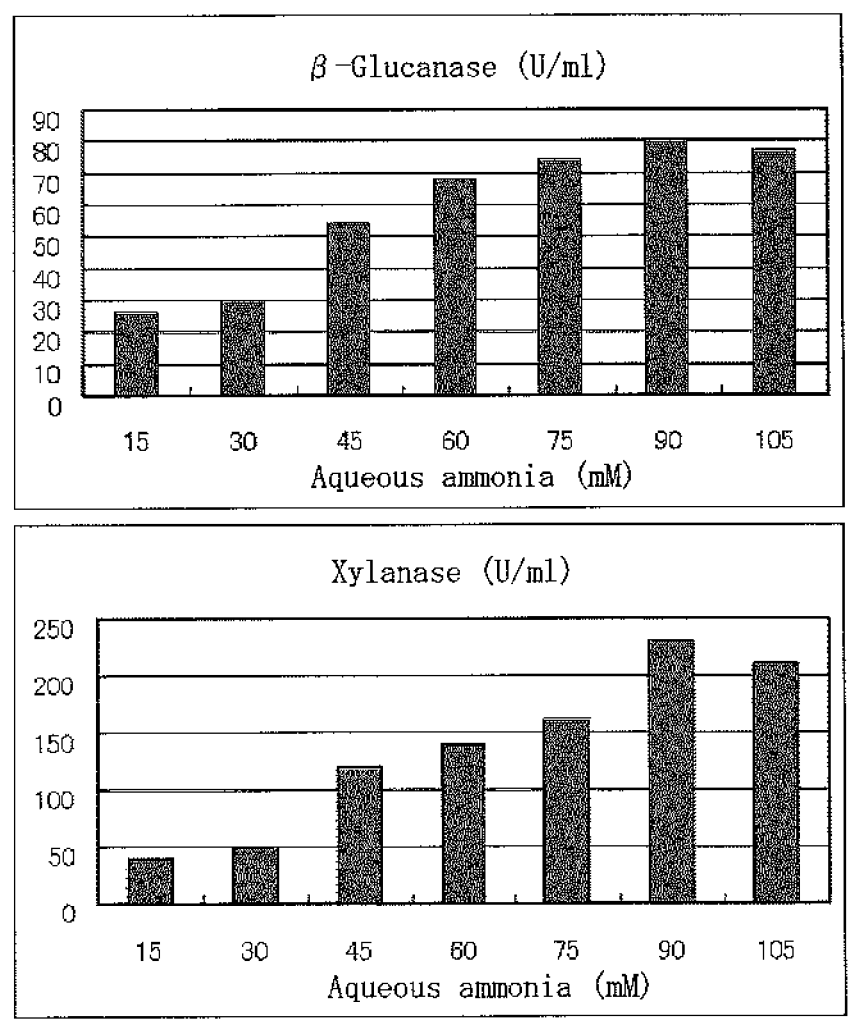
FIG. 7 A graph showing the change of enzyme activity of a culture supernatant fluid against the concentration of ammonia in a culture medium with 3% of copy paper.
Figure 8:
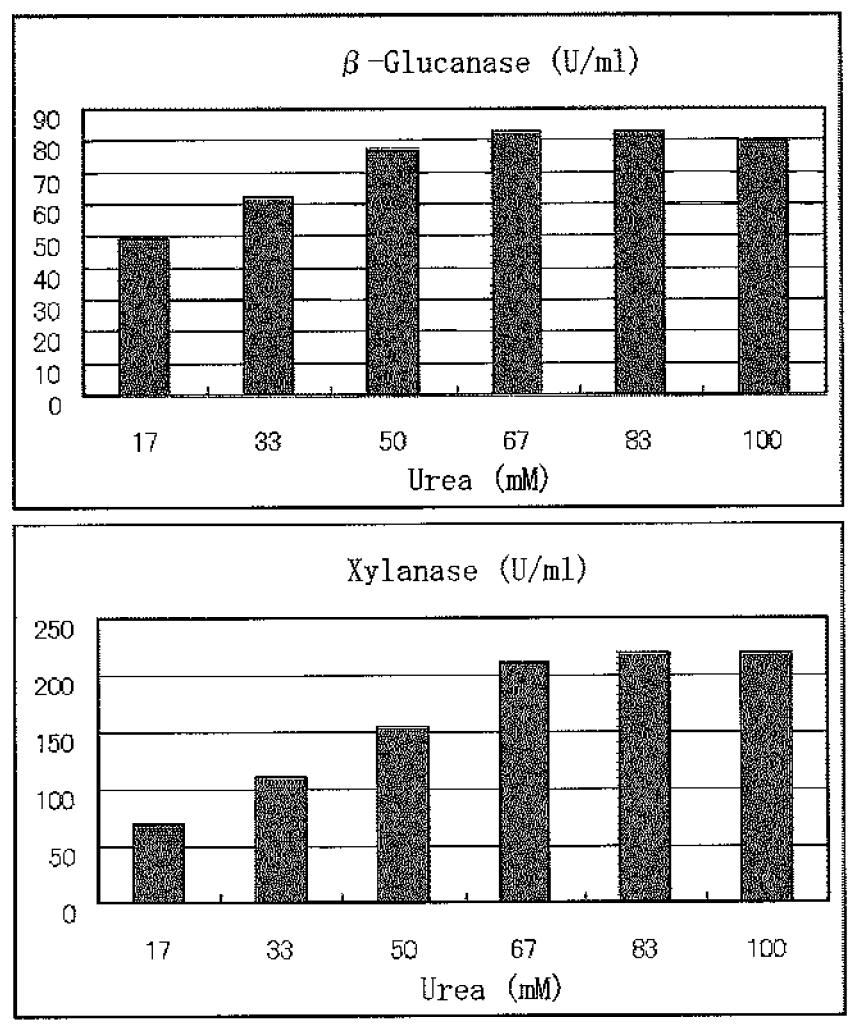
FIG. 8 A graph showing the change of enzyme activity of a culture supernatant fluid against the concentration of urea in a culture medium with 3% of copy paper.
Figure 9:
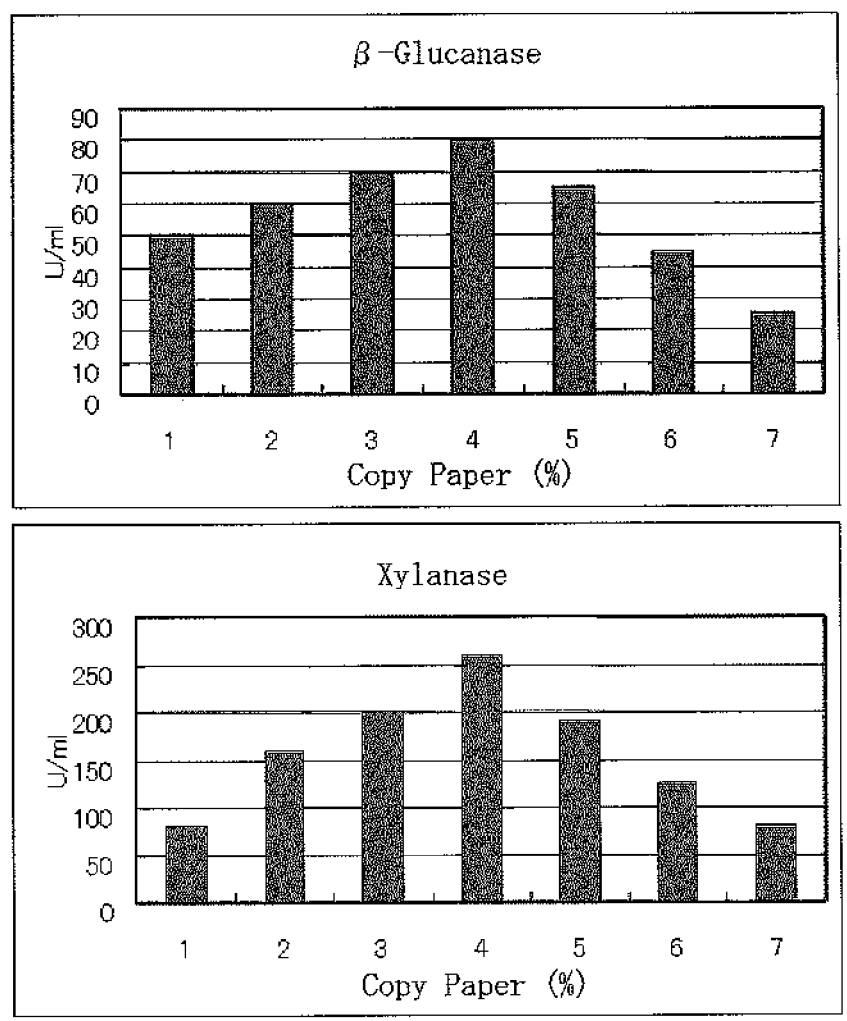
FIG. 9 A graph showing the change of enzyme activity of a culture supernatant fluid against the concentration of copy paper in a culture medium with 80 mM ammonium sulfate.
Figure 10:
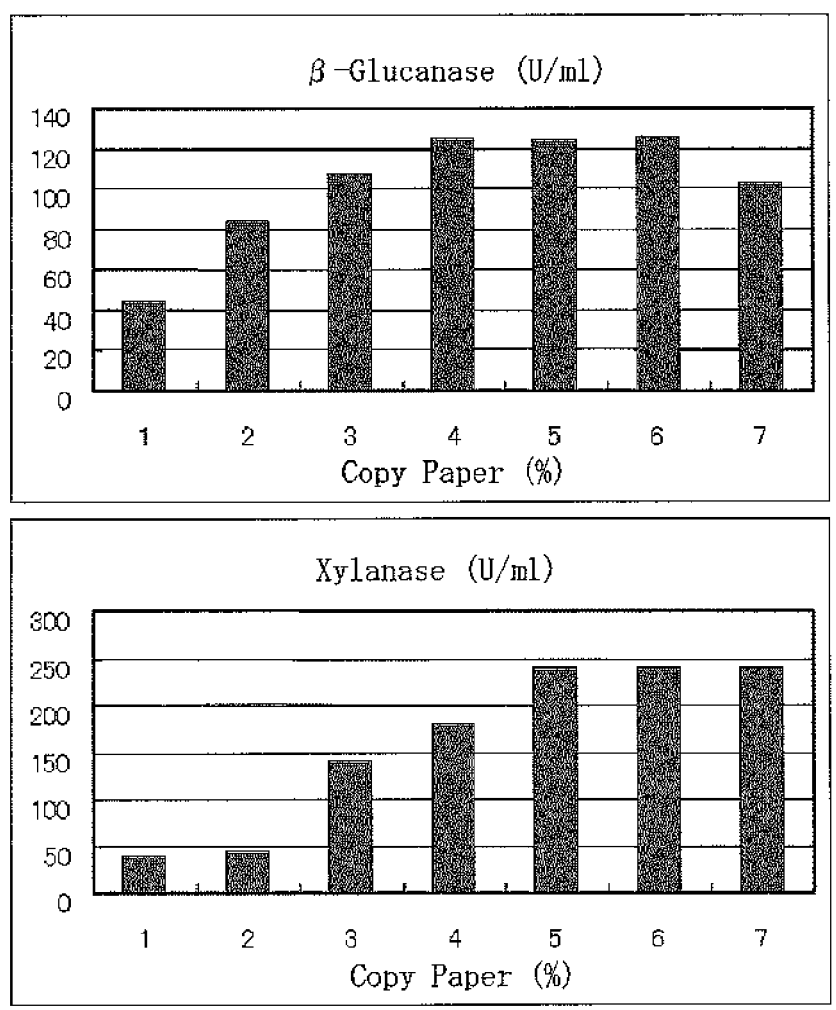
FIG. 10 A graph showing the change of enzyme activity of a culture supernatant fluid against the concentration of copy paper in a culture medium with 160 mM ammonium sulfate.
Figure 11:
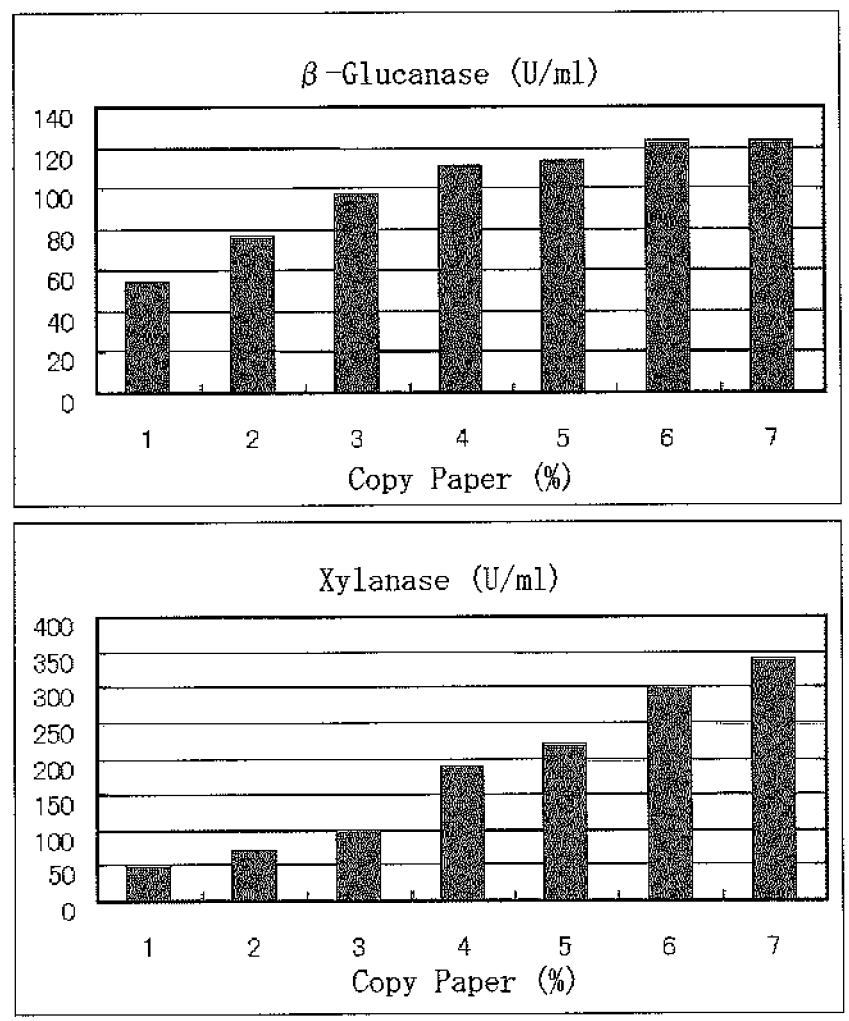
FIG. 11 A graph showing the change of enzyme activity of a culture supernatant fluid against the concentration of copy paper in a culture medium with 320 mM ammonium sulfate.
Figure 12:
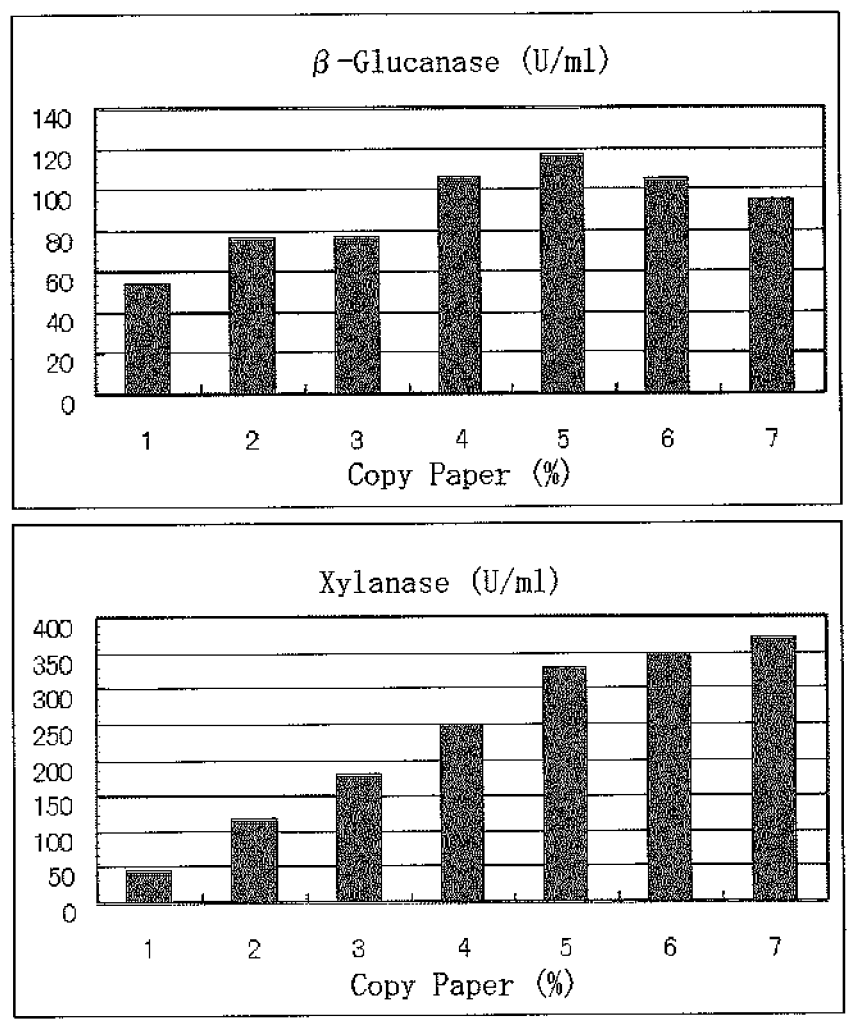
FIG. 12 A graph showing the change of enzyme activity of a culture supernatant fluid against the concentration of copy paper in a culture medium with 480 mM ammonium sulfate.
Figure 13:
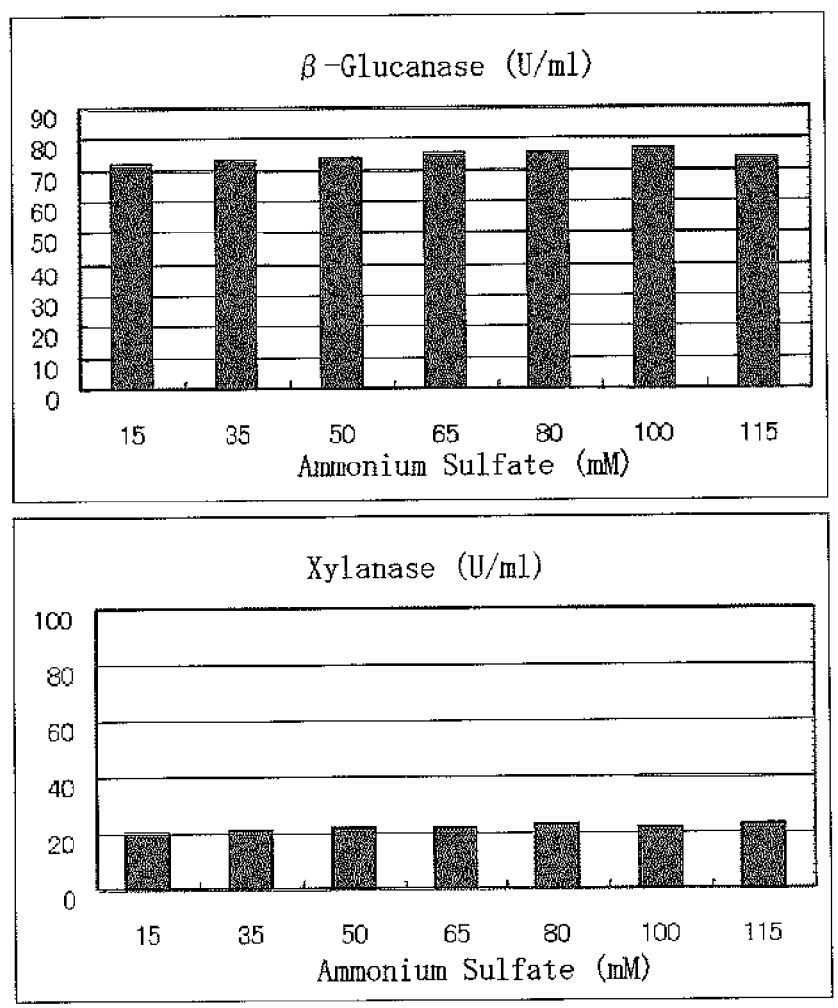
FIG. 13 A graph showing the change of enzyme activity of a culture supernatant fluid against the concentration of ammonium sulfate in a culture medium with 1% of Avicel.
Figure 14:
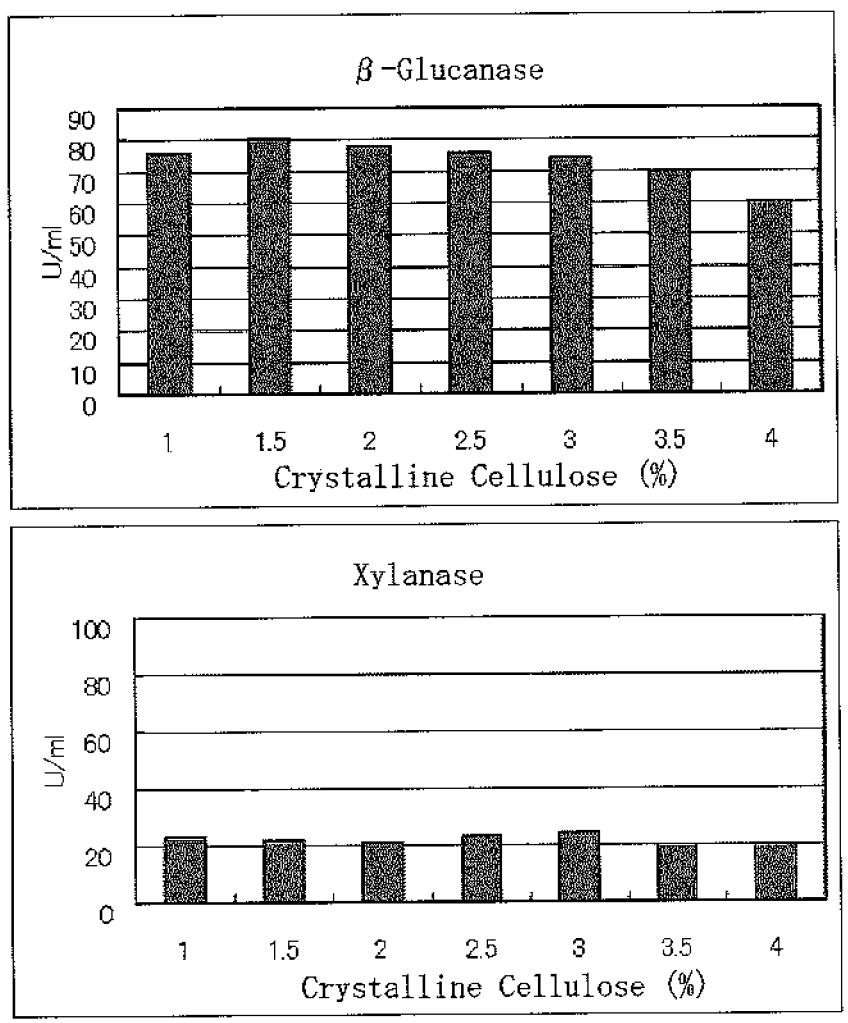
FIG. 14 A graph showing the change of enzyme activity of a culture supernatant fluid against the concentration of Avicel in a culture medium with 160 mM ammonium sulfate.
Figure 15:
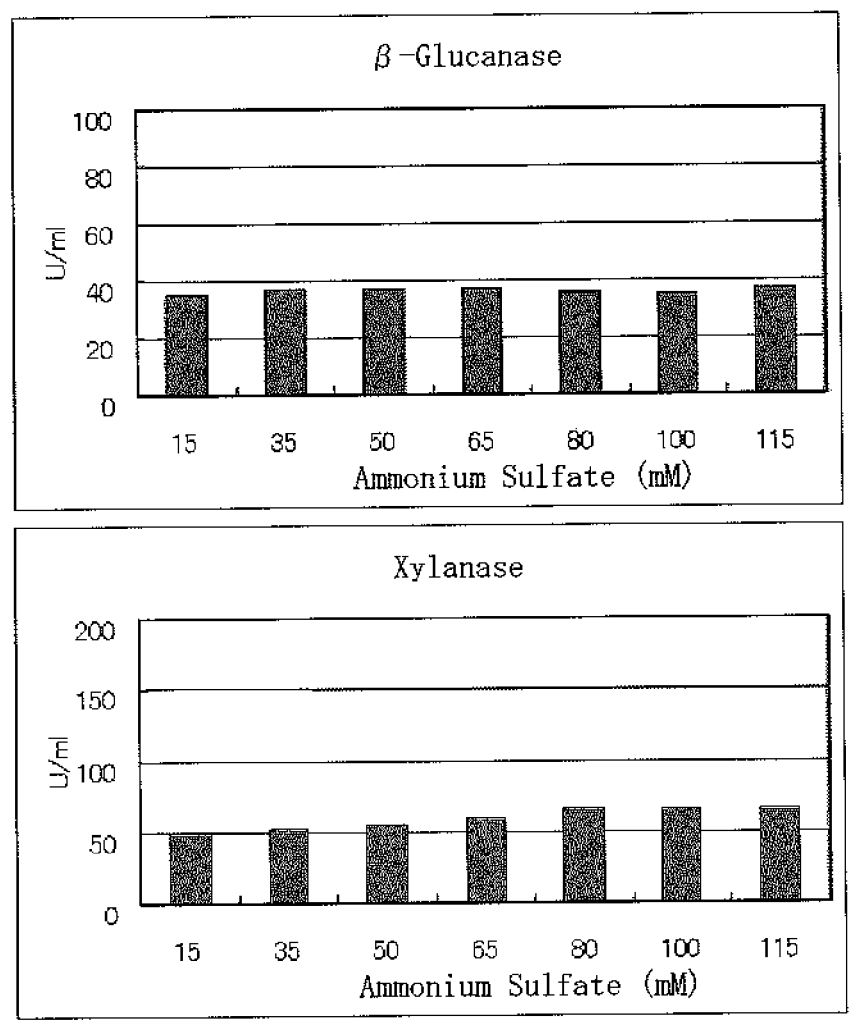
FIG. 15 A graph showing the change of enzyme activity of a culture supernatant fluid against the concentration of ammonium sulfate in a culture medium with 1% of copy paper.
Figure 16:
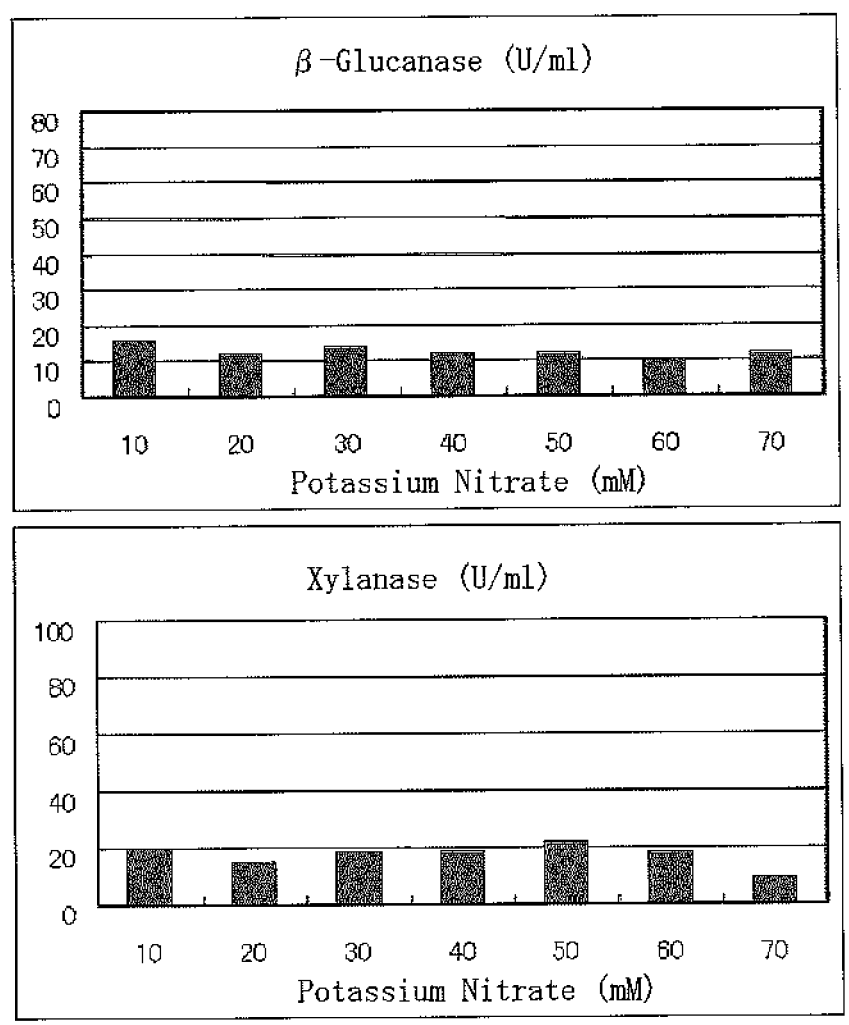
FIG. 16 A graph showing the change of enzyme activity of a culture supernatant fluid against the concentration of potassium nitrate in a culture medium with 3% of copy paper.
Figure 17:
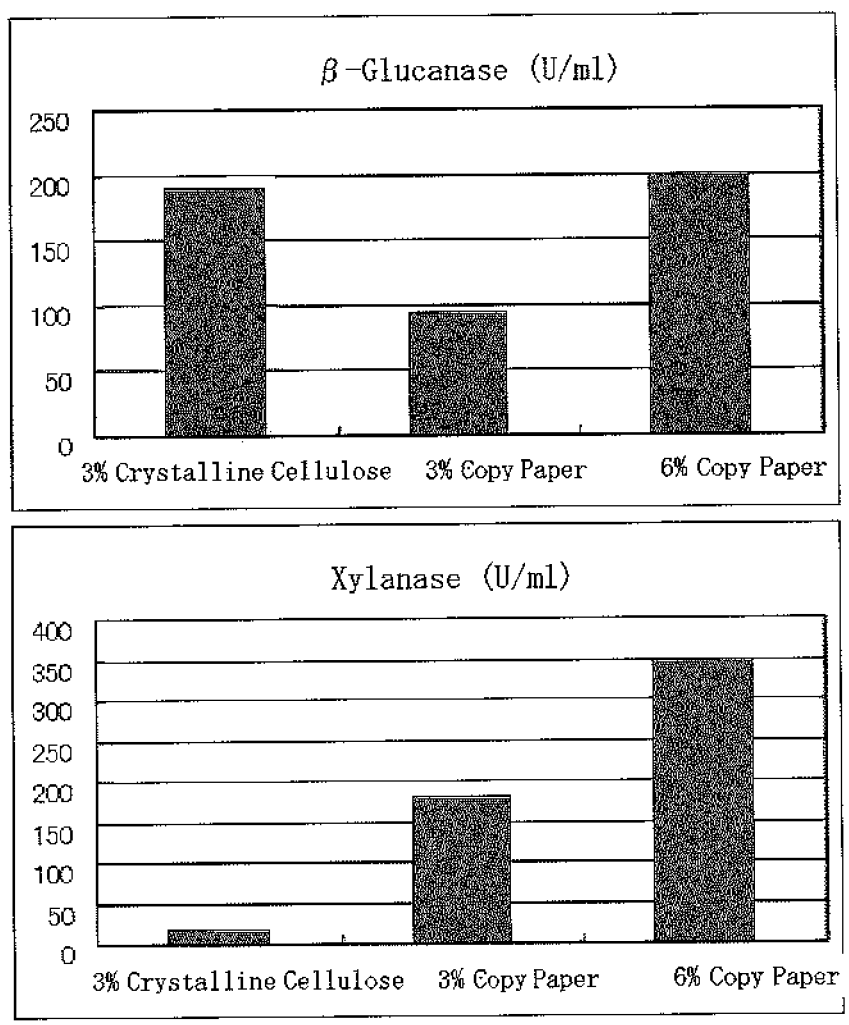
FIG. 17 A graph showing the change of enzyme activity of a culture supernatant fluid against the type of carbon source in a culture medium with 200 mM ammonium sulfate.
Figure 18:
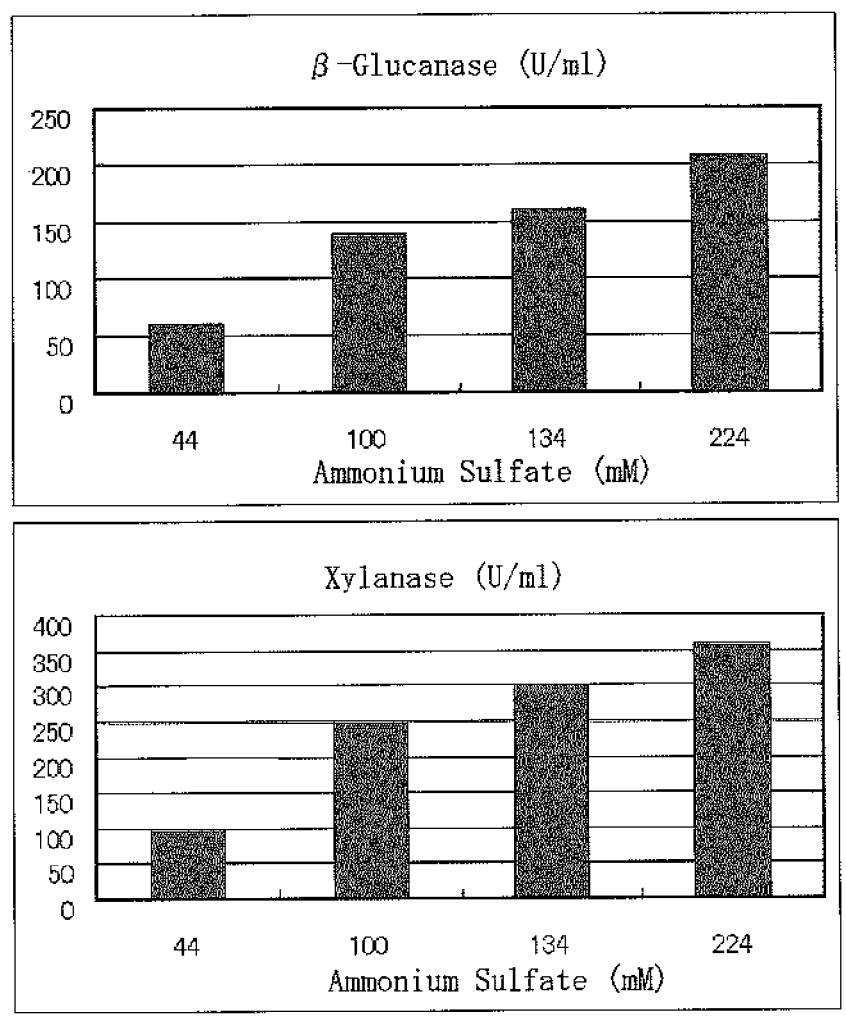
FIG. 18 A graph showing the change of enzyme activity of a culture supernatant fluid against the concentration of ammonium sulfate in a culture medium with 6% of used copy paper.
Figure 19:
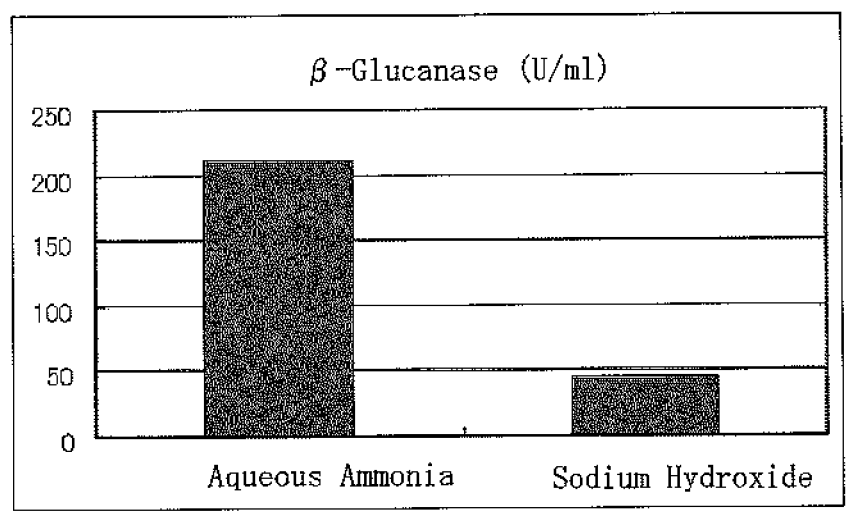
FIG. 19 A graph showing the change of enzyme activity of a culture supernatant fluid against the type of chemical for adjusting pH in a culture medium with 6% of used copy paper and 45 mM ammonium sulfate.
Figure 19:
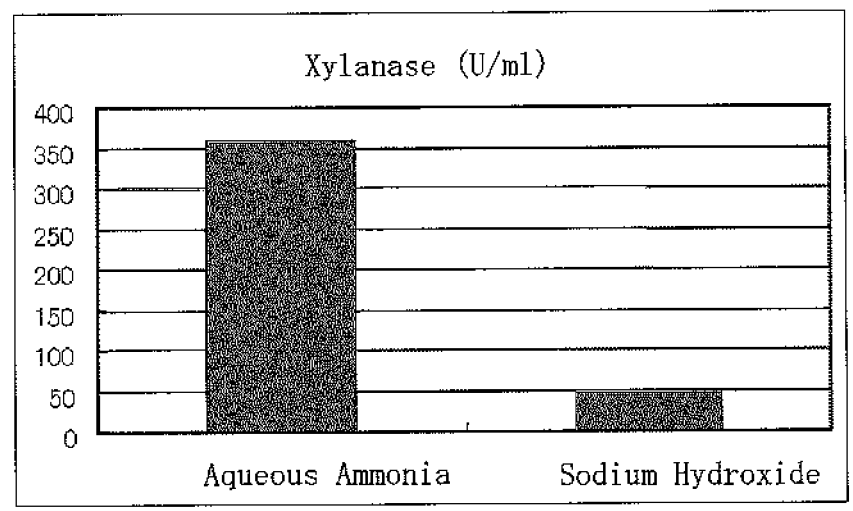
Figure 20:
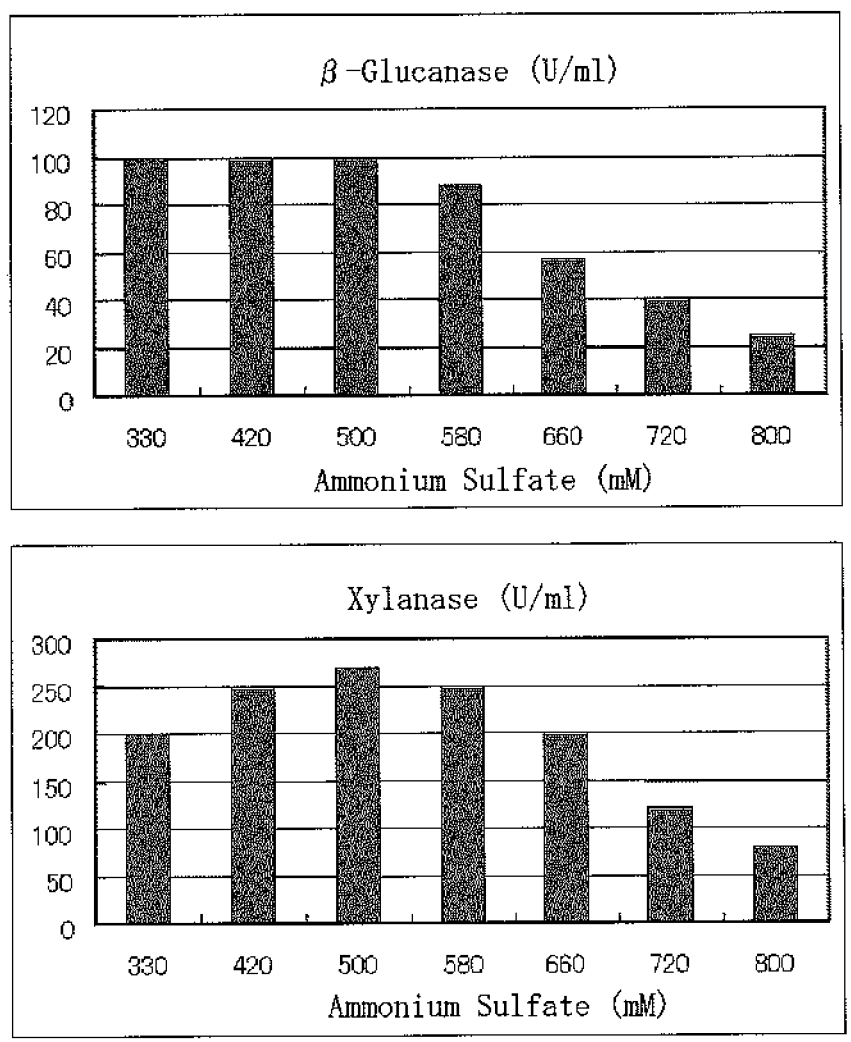
FIG. 20 A graph showing the change of enzyme activity of a culture supernatant fluid against the concentration of ammonium sulfate in a culture medium with 3% of copy paper.
Figure 21:
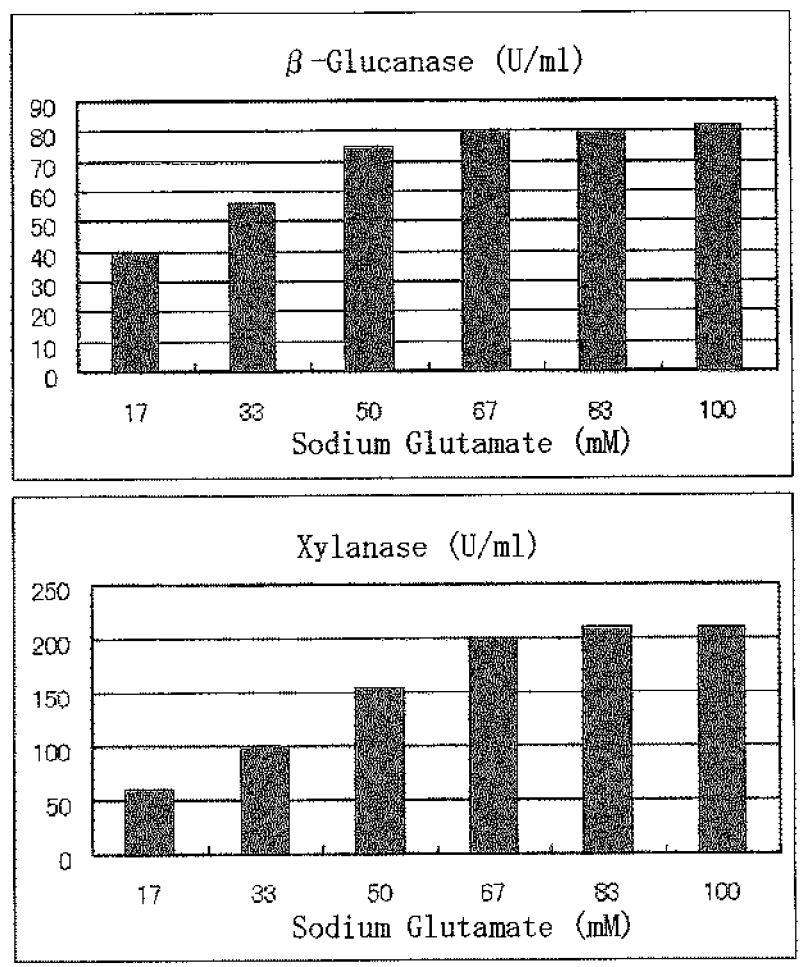
FIG. 21 A graph showing the change of enzyme activity of a culture supernatant fluid against the concentration of sodium glutamate in a culture medium with 3% of copy paper.
Figure 22:
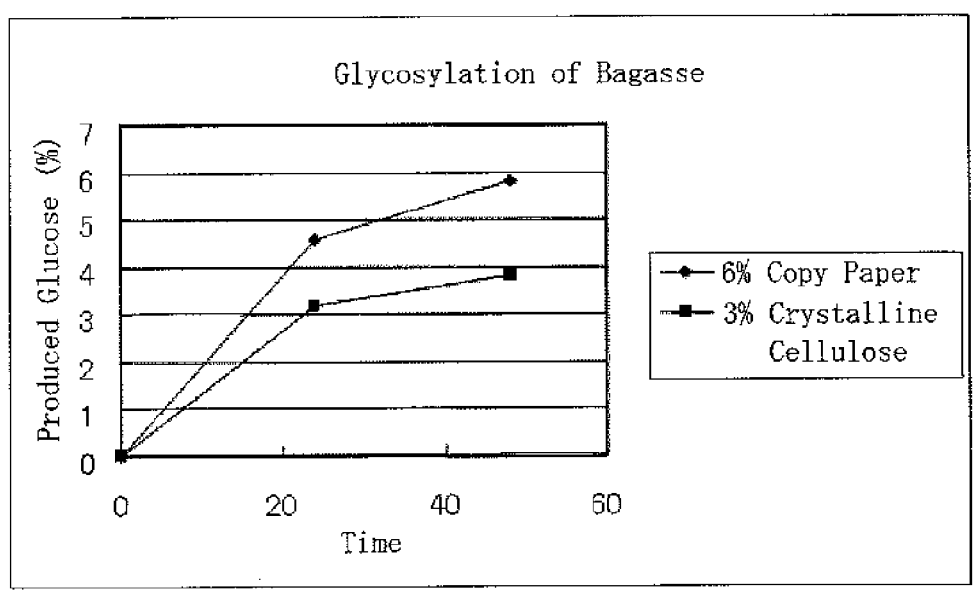
FIG. 22 A graph comparing concentration of the produced glucose when bagasse is glycosylated using each supernatant fluid of the culture medium with 6% of copy paper and the culture medium with 3% of crystalline cellulose obtained in Example 13.
Figure 23:
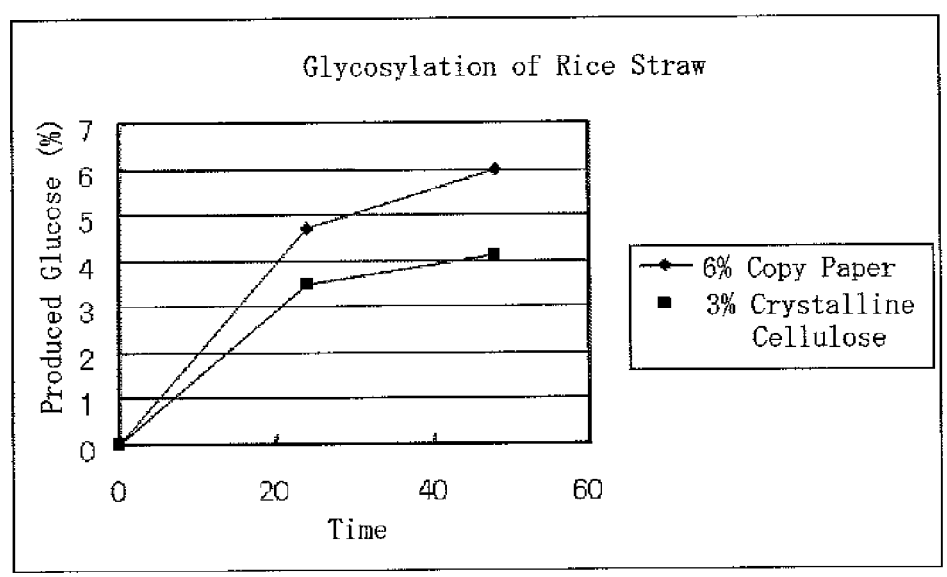
FIG. 23 A graph comparing concentration of the produced glucose when rice straw is glycosylated using each supernatant fluid of the culture medium with 6% of copy paper and the culture medium with 3% of crystalline cellulose obtained in Example 13.
Figure 24:
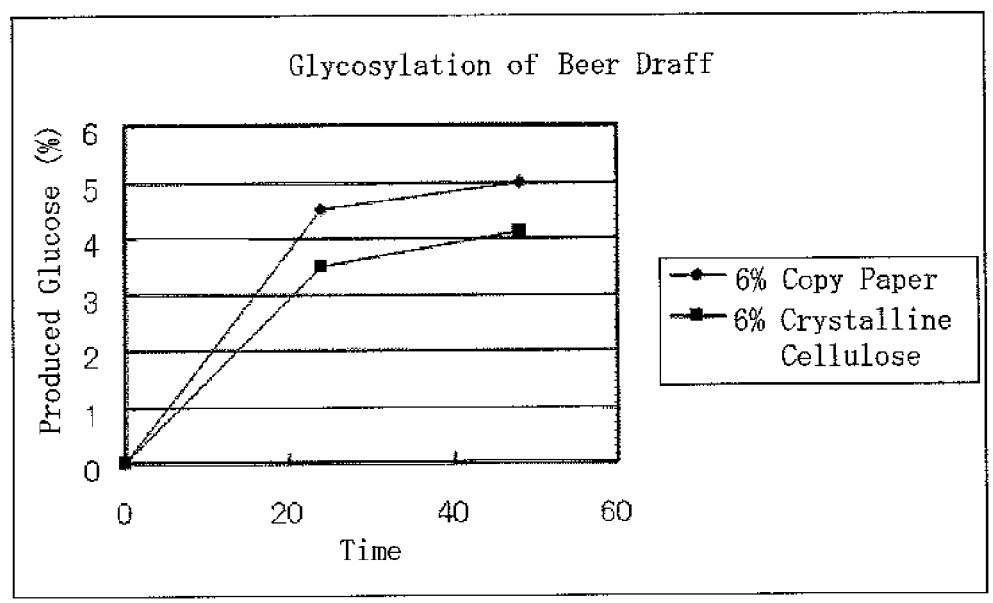
FIG. 24 A graph comparing concentration of the produced glucose when beer draff is glycosylated using each supernatant fluid of the culture medium with 6% of copy paper and the culture medium with 3% of crystalline cellulose obtained in Example 13.
Figure 25:
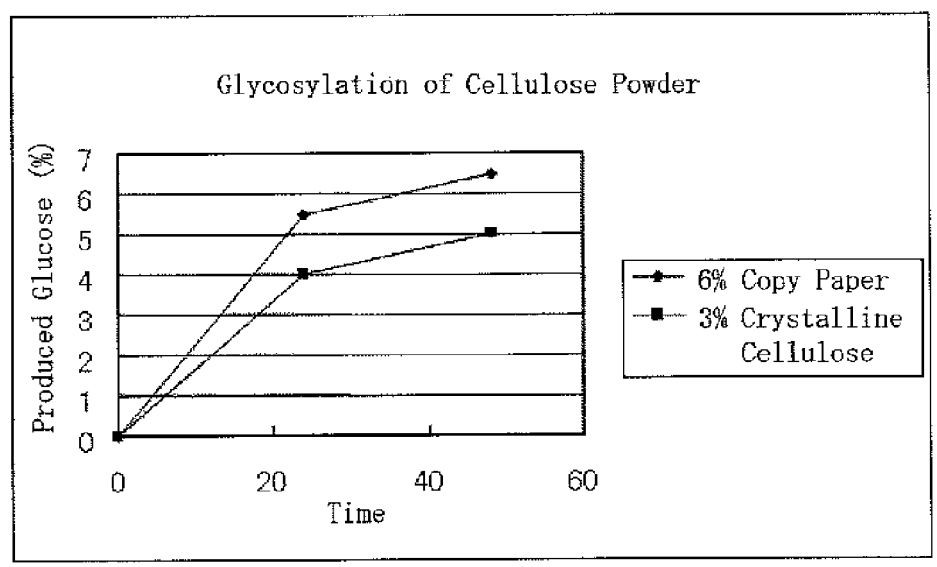
FIG. 25 A graph comparing concentration of the produced glucose when cellulose powder is glycosylated using each supernatant fluid of the culture medium with 6% of copy paper and the culture medium with 3% of crystalline cellulose obtained in Example 13.

The invention claimed is:

1. A method for producing β-glucanase and xylanase comprising the step of culturing *Trichoderma reesei* in a liquid culture medium containing (a) a pulp derived from paper which has not been subjected to heat treatment nor alkali treatment as a carbon source and (b) an ammonia nitrogen or an amino nitrogen as a nitrogen source, wherein the concentration of the ammonia nitrogen or amino nitrogen in the liquid culture medium is from 35-660 mM.

2. The method for producing β-glucanase and xylanase according to claim 1, wherein the concentration of the pulp in the liquid culture medium is not less than 2% W/V.

3. The method for producing β-glucanase and xylanase according to claim 1, wherein the initial concentration of the pulp in the liquid culture medium is from 2 to 7% W/V.

4. The method for producing β-glucanase and xylanase according to claim 1, wherein the concentration of the ammonia nitrogen or amino nitrogen in the liquid culture medium is not less than 35 mM.

5. The method for producing β-glucanase and xylanase according to claim 1, wherein the initial concentration of the ammonia nitrogen or amino nitrogen in the liquid culture medium is from 50-660 mM.

6. The method for producing β-glucanase and xylanase according to claim 1, wherein the paper is at least one selected from the group consisting of high-quality paper, groundwood paper, copy paper, newspaper and cardboard.

7. The method for producing β-glucanase and xylanase according to claim 1, wherein the pulp is added to the liquid culture medium in the course of culture.

8. The method for producing β-glucanase and xylanase according to claim 1, wherein the concentration of the pulp in the liquid culture medium is from 3 to 20% (W/V).

* * * * *